(12) United States Patent
Nettekoven et al.

(10) Patent No.: US 7,351,708 B2
(45) Date of Patent: Apr. 1, 2008

(54) PYRROLO [2,3-B] PYRIDINE DERIVATIVES

(75) Inventors: Matthias Nettekoven, Grenzach-Wyhlen (DE); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/634,563

(22) Filed: Dec. 6, 2006

(65) Prior Publication Data

US 2007/0142358 A1  Jun. 21, 2007

(30) Foreign Application Priority Data

Dec. 16, 2005  (EP)  ................. 05112317

(51) Int. Cl.
*A61K 31/5377* (2006.01)
*A61K 31/496* (2006.01)
*A61K 31/55* (2006.01)
*C07D 487/04* (2006.01)

(52) U.S. Cl. ............ 514/235.8; 514/217.05; 514/253.04; 540/599; 544/121; 544/362

(58) Field of Classification Search ............ None
See application file for complete search history.

(56) References Cited

U.S. PATENT DOCUMENTS

| | | |
|---|---|---|
| 4,598,089 A | 7/1986 | Hadvary et al. |
| 4,931,463 A | 6/1990 | Barbier et al. |
| 4,983,746 A | 1/1991 | Barbier et al. |
| 5,175,186 A | 12/1992 | Barbier et al. |
| 5,246,960 A | 9/1993 | Barbier et al. |
| 5,399,720 A | 3/1995 | Karpf et al. |
| 6,004,996 A | 12/1999 | Shah et al. |
| 2004/0176598 A1 | 9/2004 | Dugar |

FOREIGN PATENT DOCUMENTS

| | | |
|---|---|---|
| EP | 0 189 577 | 12/1989 |
| EP | 0 185 359 | 12/1991 |
| EP | 0 524 495 | 10/1996 |
| EP | 0 443 449 | 5/1997 |
| WO | WO 99/34786 | 7/1999 |
| WO | WO 00/09122 | 2/2000 |
| WO | WO 00/09123 | 2/2000 |
| WO | WO 00/44753 | 8/2000 |
| WO | WO 03/064423 | 8/2003 |
| WO | WO 2004/035556 | 4/2004 |
| WO | WO 2004/104001 | 12/2004 |
| WO | WO 2005/097740 | 10/2005 |

OTHER PUBLICATIONS

Phillips et al. Annual Reports in medicinal Chemistry, vol. 33,p. 31-40 (1998).*
Passani et al. Neuroscience and Biobehavioral Reviews, vol. 24, p. 107-113 (2000).*
Leurs et al. TIPS, vol. 19, p. 177-183 (1998).*
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
W.W.K.R. Mederski et. al, Tetrahedron, 1999, 55, 12757.
Takahashi, K, Tokita, S., Kotani, H. (2003) J. Pharmacol. Exp. Therapeutics 307, 213-218.
Cheng, Y, Prusoff, WH (1973) Biochem Pharmacol 22, 3099-3108.
Stark H., Exp Opin on Thera, V.13, N.6 (2003) 851-865.

* cited by examiner

*Primary Examiner*—Emily Bernhardt
(74) *Attorney, Agent, or Firm*—George W. Johnston; Dennis P. Tramaloni; Samuel H. Megerditchian

(57) ABSTRACT

The present invention relates to compounds of formula I

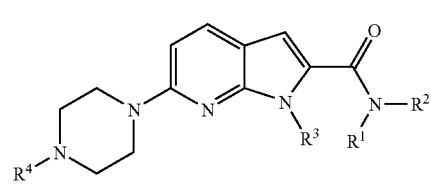

wherein $R^1$ to $R^4$ are as defined in the description and claims, and pharmaceutically acceptable salts thereof. The compounds are useful for the treatment and/or prevention of diseases which are associated with the modulation of H3 receptors.

14 Claims, No Drawings

PYRROLO [2,3-B] PYRIDINE DERIVATIVES

PRIORITY TO RELATED APPLICATIONS

This application claims the benefit of European Application No. 05112317.2, filed Dec. 16, 2005, which is hereby incorporated by reference in its entirety.

FIELD OF THE INVENTION

The present invention is directed to novel 6-piperazinyl-1H-pyrrolo[2,3-b] pyridine derivatives, their manufacture, pharmaceutical compositions containing them and their use as medicaments. The active compounds of the present invention are useful in treating obesity and other disorders.

In particular, the present invention is directed to compounds of the general formula

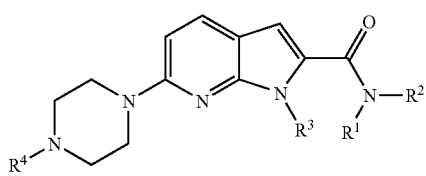

I and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrick, Br. J. Pharmacol. 1982, 107, 919-923; Blandina et al. in The Histamine H3 Receptor (Leurs RL and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

Therefore, there is a need for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In an embodiment of the present invention, provided is a compound of formula I:

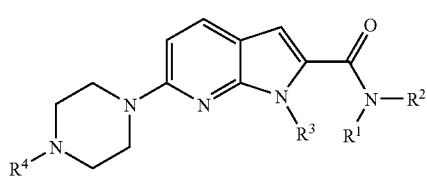

I wherein:

R¹ is selected from the group consisting of
  lower alkyl, lower alkenyl, lower alkinyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups;

$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of hydrogen, lower alkyl, lower hydroxyalkyl, lower alkoxyalkyl, lower halogenalkyl, lower cycloalkylalkyl, lower alkanoyl, lower cyanoalkyl, lower alkylsulfonyl,
phenylsulfonyl wherein the phenyl ring may be unsubstituted or substituted with one or two groups independently selected from lower alkyl, halogen, lower alkoxy, lower halogenalkoxy and lower hydroxyalkyl,
phenyl unsubstituted or substituted with one or two groups independently selected from lower alkyl, halogen, lower alkoxy, lower halogenalkoxy and lower hydroxyalkyl, lower phenylalkyl, wherein the phenyl ring may be unsubstituted or substituted with one or two groups independently selected from lower alkyl, halogen, lower alkoxy, lower halogenalkoxy and lower hydroxyalkyl, and heteroaryl unsubstituted or substituted with one or two groups independently selected from lower alkyl or halogen;

$R^4$ is lower alkyl or cycloalkyl; and pharmaceutically acceptable salts thereof.

In another embodiment of the present invention, provided is a process for the manufacture of compounds according to claim 1, comprising the steps of:

coupling a compound of formula II

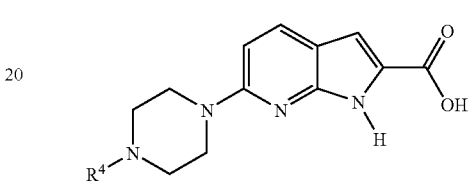

wherein $R^4$ is as defined above, with an amine of the formula III

   III wherein $R^1$ and $R^2$ are as defined above, under basic conditions to obtain a compound of the formula IA

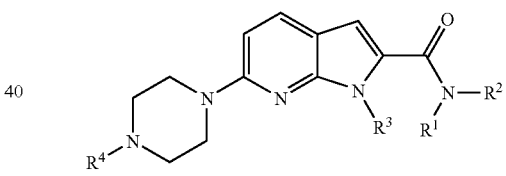

wherein $R^3$ is hydrogen, and optionally transferring into a compound of formula IB

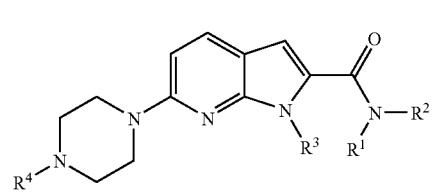

wherein $R^3$ is a group as defined above other than hydrogen, and if desired, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically active amount of a compound according to formula I to a human being or animal in need thereof.

In a still further embodiment of the present invention, provided is a method for the treatment or prevention of obesity in a human being or animal, which method comprises administering a therapeutically effective amount of a compound according to any one of formula I in combination or association with a therapeutically effective amount of a compound selected from the group consisting of a lipase inhibitor, an anorectic agent, a selective serotonin reuptake inhibitor, and an agent that stimulates metabolism of body fat, to said human being or animal in need thereof.

In a yet still another embodiment of the present invention, provided is a method of treatment or prevention of type II diabetes in a human being or animal, which comprises administering a therapeutically effective amount of a compound claim 1 in combination or association with a therapeutically effective amount of an anti-diabetic agent to said human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-8}$-alkinyl", alone or in combination, signifies a straight-chain or branched hydrocarbon residue comprising a triple bond and up to 8, preferably up to 6, particularly preferred up to 4 carbon atoms. Examples of alkinyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred is cyclopentyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "lower phenylsulfonyl" means the group "phenyl-S(O)$_2$—".

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group —CO—NH$_2$.

The term "dialkylcarbamoyl" refers to the group —CO—NR'R", wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group, preferably dimethylcarbamoyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are pyridyl, thiazolyl and oxazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. A preferred heterocyclyl group is piperidinyl or tetrahydropyranyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. A "4-, 5-, 6- or 7-membered saturated or partly unsaturated heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl. The heterocyclic ring may also be condensed with a phenyl ring, said phenyl ring being unsubstituted or substituted by one, two or three groups independently selected from lower alkyl, lower alkoxy and halogen. Examples for such condensed heterocyclic rings are 3,4-dihydro-1H-isoquinoline or 1,3-dihydroisoindole.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

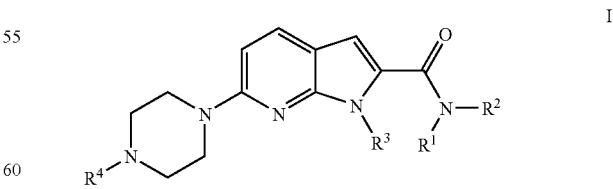

I wherein

R$^1$ is selected from the group consisting of
  lower alkyl, lower alkenyl, lower alkinyl,
  cycloalkyl, lower cycloalkylalkyl, lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl,
halogen, lower alkoxy and lower hydroxyalkyl,
lower heterocyclyl wherein the heterocyclyl ring may be unsubstituted or substituted with one or two lower alkyl groups, and
lower heterocyclylalkyl wherein the heterocyclyl ring may be unsubstituted or substituted with one or two lower alkyl groups;

$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl,
lower heterocyclyl wherein the heterocyclyl ring may be unsubstituted or substituted with one or two lower alkyl groups, and
lower heterocyclylalkyl wherein the heterocyclyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of hydrogen, lower alkyl, lower hydroxyalkyl, lower alkoxyalkyl, lower halogenalkyl, lower cycloalkylalkyl, lower alkanoyl, lower cyanoalkyl, lower alkylsulfonyl, phenylsulfonyl wherein the phenyl ring may be unsubstituted or substituted with one or two groups independently selected from lower alkyl, halogen, lower alkoxy, lower halogenalkoxy and lower hydroxyalkyl,
phenyl unsubstituted or substituted with one or two groups independently selected from lower alkyl, halogen, lower alkoxy, lower halogenalkoxy and lower hydroxyalkyl,
lower phenylalkyl, wherein the phenyl ring may be unsubstituted or substituted with one or two groups independently selected from lower alkyl, halogen, lower alkoxy, lower halogenalkoxy and lower hydroxyalkyl, and
heteroaryl unsubstituted or substituted with one or two groups independently selected from lower alkyl or halogen;

$R^4$ is lower alkyl or cycloalkyl;

and pharmaceutically acceptable salts thereof.

Preferred compounds of formula I of the present invention are compounds of formula I, wherein $R^1$ is selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups;

and $R^2$ is hydrogen or lower alkyl.

More preferred are those compounds of formula I, wherein $R^1$ is lower alkyl or cycloalkyl, with those compounds, wherein $R^1$ is selected from the group consisting of ethyl, n-propyl and i-propyl, or with those compounds, wherein $R^1$ is cyclopentyl or cyclohexyl, being especially preferred.

Furthermore, compounds of formula I according to the present invention are preferred, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Within this group, those compounds are preferred, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenalkyl, cyano, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Especially preferred are those compounds of formula I, wherein $R^1$ and $R^2$ together with the nitrogen atom to which they are attached form a heterocyclic ring selected from the group consisting of pyrrolidine, piperidine, morpholine and azepane, wherein said heterocyclic ring is unsubstituted or substituted by one, two or three groups independently selected from lower alkyl, halogen, halogenalkyl, cyano, hydroxy, lower alkoxy, oxo, phenyl, benzyl, pyridyl and carbamoyl.

More preferably, $R^1$ and $R^2$ together with the nitrogen atom to which they are attached form a heterocyclic ring selected from the group consisting of pyrrolidine, 3-hydroxypyrrolidine, 2-cyanopyrrolidine, 2-iospropylpyrrolidine, morpholine, piperidine, 3-methylpiperidine, 2-methylpiperidine, 3,5-dimethylpiperidine, 3,3-difluoropiperidine, 4,4-difluoropiperidine, 4-methoxypiperidine, 3-hydroxypiperidine and azepane.

Furthermore, compounds of formula I according to the present invention are preferred, wherein $R^3$ is selected from the group consisting of hydrogen, lower alkyl, lower halogenalkyl, lower cycloalkylalkyl and lower cyanoalkyl.

Especially preferred are compounds of formula I, wherein $R^3$ is hydrogen.

Also preferred are compounds of formula I according to the present invention, wherein $R^4$ is cycloalkyl. Especially preferred are those compounds of formula I, wherein $R^4$ is cyclopentyl.

Further preferred compounds of formula I according to the invention are those, wherein $R^4$ is lower alkyl, with those compounds, wherein $R^4$ is isopropyl, being especially preferred.

Preferred compounds of formula I of the present invention are the following:

[6-(4-cyclopentyl-piperazin-1-yl)-1H-pyrrolo[2,3-b]pyridin-2-yl]-piperidin-1-yl-methanone,

[6-(4-cyclopentyl-piperazin-1-yl)-1H-pyrrolo[2,3-b]pyridin-2-yl]-pyrrolidin-1-yl-methanone,

[6-(4-cyclopentyl-piperazin-1-yl)-1H-pyrrolo[2,3-b]pyridin-2-yl]-(3-methyl-piperidin-1-yl)-methanone, 6-(4-cyclopentyl-piperazin-1-yl)-1H-pyrrolo[2,3-b]pyridine-2-carboxylic acid cyclohexylamide, azepan-1-yl-[6-(4-cyclopentyl-piperazin-1-yl)-1H-pyrrolo[2,3-b]pyridin-2-yl]-methanone,

[6-(4-cyclopentyl-piperazin-1-yl)-1H-pyrrolo[2,3-b]pyridin-2-yl]-(2-methyl-piperidin-1-yl)-methanone, 6-(4-cyclopentyl-piperazin-1-yl)-1H-pyrrolo[2,3-b]pyridine-2-carboxylic acid cyclopentylamide,

[6-(4-cyclopentyl-piperazin-1-yl)-1H-pyrrolo[2,3-b]pyridin-2-yl]-(3-hydroxy-pyrrolidin-1-yl)-methanone,

[6-(4-cyclopentyl-piperazin-1-yl)-1H-pyrrolo[2,3-b]pyridin-2-yl]-(3,5-dimethyl-piperidin-1-yl)-methanone, 6-(4-cyclopentyl-piperazin-1-yl)-1H-pyrrolo[2,3-b]pyridine-2-carboxylic acid propylamide, (S)-1-[6-(4-cyclopentyl-piperazin-1-yl)-1H-pyrrolo[2,3-b]pyridine-2-carbonyl]-pyrrolidine-2-carbonitrile, 6-(4-cyclopentyl-piperazin-1-yl)-1H-pyrrolo[2,3-b]pyridine-2-carboxylic acid cyclohexyl-isopropyl-amide,

[6-(4-cyclopentyl-piperazin-1-yl)-1H-pyrrolo[2,3-b]pyridin-2-yl]-morpholin-4-yl-methanone,

[6-(4-cyclopentyl-piperazin-1-yl)-1H-pyrrolo[2,3-b]pyridin-2-yl]-(2-isopropyl-pyrrolidin-1-yl)-methanone,

[6-(4-cyclopentyl-piperazin-1-yl)-1H-pyrrolo[2,3-b]pyridin-2-yl]-(4-methyl-piperidin-1-yl)-methanone,

[6-(4-cyclopentyl-piperazin-1-yl)-1H-pyrrolo[2,3-b]pyridin-2-yl]-(4,4-difluoro-piperidin-1-yl)-methanone,

[6-(4-cyclopentyl-piperazin-1-yl)-1H-pyrrolo[2,3-b]pyridin-2-yl]-(3,3-difluoro-piperidin-1-yl)-methanone,

[6-(4-cyclopentyl-piperazin-1-yl)-1H-pyrrolo[2,3-b]pyridin-2-yl]-(4-methoxy-piperidin-1-yl)-methanone,

[6-(4-cyclopentyl-piperazin-1-yl)-1H-pyrrolo[2,3-b]pyridin-2-yl]-(3-hydroxy-piperidin-1-yl)-methanone, 6-(4-cyclopentyl-piperazin-1-yl)-1H-pyrrolo[2,3-b]pyridine-2-carboxylic acid diethylamide, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises coupling a compound of formula II

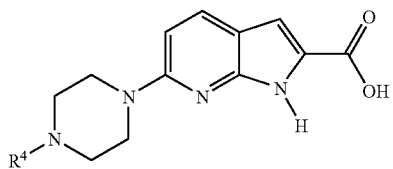

II wherein R⁴ is as defined herein before, with an amine of the formula III

H—NR¹R²     III wherein R¹ and R² are as defined herein before, under basic conditions to obtain a compound of the formula IA

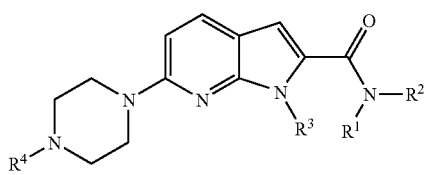

IA wherein R³ is hydrogen, and optionally transferring into a compound of formula IB

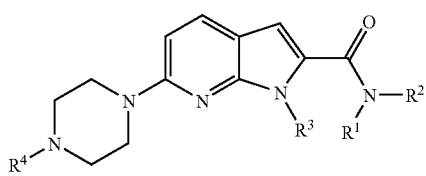

IB wherein R³ is a group as defined herein before other than hydrogen, and if desired, converting the compound obtained into a pharmaceutically acceptable acid addition salt.

Transferring into a compound of formula IB means treating the compound of formula IA with a suitable base in a suitable solvent under anhydrous conditions (e.g. sodium hydride in DMF) and reacting the intermediate anion with an alkylating or acylating agent R¹—X, wherein X signifies a leaving group such as e.g. iodide, bromide, methanesulfonate or chloride, to obtain a compound of formula IB wherein R¹ signifies lower alkyl, lower hydroxyalkyl, lower alkoxyalkyl, lower halogenalkyl, lower hydroxyhalogenalkyl, lower cycloalkylalkyl, lower alkylcarbonyl, lower alkylsulfonyl or phenylsulfonyl.

Typical examples of an alkylating or acylating agent R³—X are methyl iodide, benzyl bromide, 2,2,2-trifluoroethyl-methanesulfonate, acetyl chloride or benzenesulfonyl chloride.

In more detail, the compounds of formula I can be manufactured by the methods given below, by the methods given in the examples or by analogous methods. The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

Starting materials are either commercially available or can be prepared by methods analogous to the methods given below, by methods described in references cited in the description or in the examples, or by methods known in the art.

The intermediates of formula II can be prepared following the procedure as depicted in scheme 1.

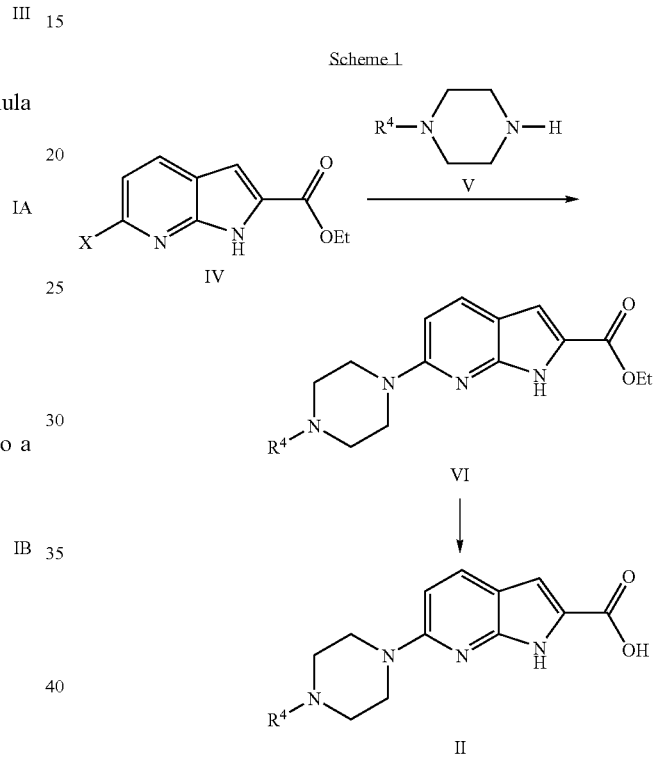

Compounds of formula IV, wherein X is halogen, can be prepared by an analogous process as described in WO 00/44753 or WO 03/064423 starting from 2-tert-butoxycarbonylamino-3-methylpyridine and diethyl oxalate. In the presence of a strong base such as, e.g. n-butyllithium, (RS) ethyl 2-hydroxy-1-tert-butoxycarbonyl-7-azaindoline-2-carboxylate is formed which is then treated with a strong acid such as, e.g. concentrated hydrochloric acid in a polar solvent such as ethanol to obtain 7-azaindole-2-carboxylic acid ethyl ester. After oxidation of the nitrogen atom in 7-position (the "pyridine nitrogen") under appropriate oxidizing conditions, such as meta-chloroperbenzoic acid in dichloromethane, the resulting N-oxide is treated with a nucleophilic system, such as methyl chloroformate or methyl bromoformate, in the presence of a suitable base, like e.g. hexamethyldisilazane in a suitable solvent such as, e.g. tetrahydrofuran. The indole nitrogen can be optionally protected in this process, preferably with a BOC (tert-butoxycarbonyl) group.

The coupling of halogeno substituted pyridine derivatives with piperazines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The compounds of formula IV can conveniently be transformed to the respective piperazinyl derivatives VI through reaction with a piperazine derivative V (either commercially available or accessible by methods described in references or by methods known in the art; as appropriate). The reaction can be carried out in the presence or the absence of a solvent and in the presence or the absence of a base. We find it convenient to carry out the reaction in a solvent like water and/or dimethylformamide (DMF) and, if necessary, in the presence of a base like triethylamine or diisopropyl-ethylamine (DIPEA). There is no particular restriction on the nature of the solvent to be employed, provided that it has no adverse effect on the reaction or the reagents involved and that it can dissolve the reagents, at least to some extent.

Examples for suitable solvents include DMF, dichloromethane (DCM), dioxane, tetrahydrofurane (THF), and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. A period of from 0.5 h to several days will usually suffice to yield piperazinyl pyridine derivatives VI.

Compounds of formula II are then obtained from piperazinyl pyridine derivatives VI by hydrolization of the ester group under basic conditions (e.g. with lithium hydroxide in polar solvents such as e.g. tetrahydrofurane, methanol or water or mixtures thereof). A period of from 12 h to 24 h at room temperature or heating the reaction mixture from ambient temperature to reflux will usually suffice to yield the carboxylic acids of formula II.

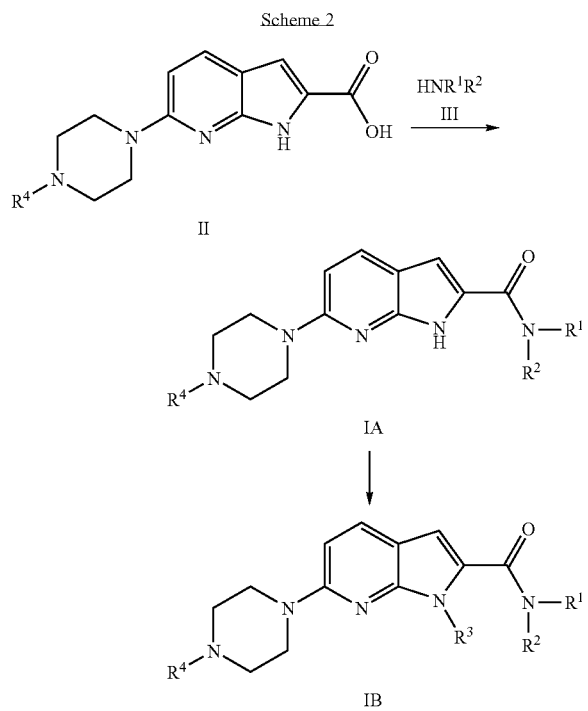

Compounds of the general formula IA and IB can be prepared according to scheme 2. The coupling of carboxylic acids II with amines III (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. dimethylformamide (DMF) or dioxane in the presence of a base (e.g. triethylamine or diisopropylethylamine).

Intermediates of formula IB can be obtained for example through treatment of intermediates of formula IA with a suitable base in a suitable solvent under anhydrous conditions (e.g. sodium hydride in DMF) and reacting the intermediate anion with an alkylating or acylating agent $R^3$—X such as, e.g. methyl iodide, 2-bromopropane, 2,2,2-trifluoroethyl-methanesulfonate, methanesulfonyl- or phenylsulfonylchloride. In those cases $R^3$ signifies a methyl, trifluoromethyl, isopropyl or an alkyl- or arylsulfonyl group and X signifies a leaving group such as, e.g. iodide, bromide, methanesulfonate or chloride. Compounds of formula IB where $R^3$ signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula IA are reacted with an optionally substituted phenylboronic acid using an appropriate catalyst (e.g. copper(II) acetate) and base (e.g. pyridine) in a suitable solvent like, e.g. dichloromethane.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, a minorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyl-dopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-Methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2$x $6H_2O$ pH 7.4. Washing Buffer: 50 mM Tris-HCl pH 7.4 and 5 mM $MgCl_2$x$6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 µl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, WH (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 1 | 48.4 |
| Example 4 | 22.7 |
| Example 8 | 83.1 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

[6-(4-Cyclopentyl-piperazin-1-yl)-1H-pyrrolo[2,3-b]pyridin-2-yl]-piperidin-1-yl-methanone Step 1: 6-(4-Cyclopentyl-piperazin-1-yl)-1H-pyrrolo[2,3-b]pyridine-2-carboxylic acid ethyl ester A mixture of 1 g (3.7 mmol) 6-bromo-1H-pyrrolo[2,3-b]pyridine-2-carboxylic acid ethyl ester (prepared according to the method described in WO 2003/064423 A1) and 2.8 g (18.6 mmol) 1-cyclopentyl-piperazine (commercially available) was heated to 140° C. for 1 h. The mixture was absorbed on isolute and purified by flash column chromatography on silica eluting with a gradient formed from n-heptane and ethyl acetate (0.1% NEt₃). Evaporation of the product fractions yielded 501 mg (39%) of the title compound as white solid. MS: (m/e): 343.4 (MH⁺).

Step 2: 6-(4-Cyclopentyl-piperazin-1-yl)-1H-pyrrolo[2,3-b]pyridine-2-carboxylic acid hydrochloride A mixture of 700 mg (2 mmol) 6-(4-cyclopentyl-piperazin-1-yl)-1H-pyrrolo[2,3-b]pyridine-2-carboxylic acid ethyl ester and 0.43 g (10 mmol) LiOHxH₂O in 10 mL THF, 5 mL methanol and 5 mL water was heated to 65° C. for 16 h. The mixture was concentrated and treated with water and HCl aq. (conc.). The precipitate was filtered off, washed with diethyl ether and dried to yield 0.63 g (88%) of the title compound as white solid. MS: (m/e): 315.3 (MH⁺).

Step 3: [6-(4-Cyclopentyl-piperazin-1-yl)-1H-pyrrolo[2,3-b]pyridin-2-yl]-piperidin-1-yl-methanone A mixture of 0.63 g (1.8 mmol) 6-(4-cyclopentyl-piperazin-1-yl)-1H-pyrrolo[2,3-b]pyridine-2-carboxylic acid; hydrochloride and 1.14 g (9 mmol) oxalyl chloride in 30 mL DCM was stirred at room temperature for 1 h. After removal of all volatiles 27.4 mg (0.08 mmol) of the residue were taken up in 2 mL DCM and treated with 20.4 mg (0.24 mmol) piperidine and 40.5 mg (0.4 mmol) NEt₃. The mixture was shaken at room temperature for 16 h. After evaporation of all volatiles the residue was taken up in a mixture of DMF/methanol/water/NEt₃ and subjected to preparative HPLC purification on reversed phase eluting with an acetonitrile/water (0.05% NEt₃) gradient. After evaporation of the product fractions 4.0 mg (13%) of the title compound was obtained.

MS (m/e): 382.4 (MH⁺).

According to the procedure described for the synthesis of Example 1 further 6-piperazinyl-1H-pyrrolo[2,3-b]pyridine derivatives have been synthesized from 6-(4-cyclopentyl-piperazin-1-yl)-1H-pyrrolo[2,3-b]pyridine-2-carboxylic acid hydrochloride (as prepared in step 2) and the respective amine mentioned in table 1. The examples are compiled in table 1 and comprise Example 2 to Example 20.

TABLE 1

| Ex. No. | MW | Chemical Name | Starting materials | MW found (MH⁺) |
|---|---|---|---|---|
| 2 | 367.5 | [6-(4-cyclopentyl-piperazin-1-yl)-1H-pyrrolo[2,3-b]pyridin-2-yl]-pyrrolidin-1-yl-methanone | 6-(4-cyclopentyl-piperazin-1-yl)-1H-pyrrolo[2,3-b]pyridine-2-carboxylic acid hydrochloride and pyrrolidine (commercially available) | 368.3 |
| 3 | 395.6 | [6-(4-cyclopentyl-piperazin-1-yl)-1H-pyrrolo[2,3-b]pyridin-2-yl]-(3-methyl-piperidin-1-yl)-methanone | 6-(4-cyclopentyl-piperazin-1-yl)-1H-pyrrolo[2,3-b]pyridine-2-carboxylic acid hydrochloride and 3-methyl-piperidine (commercially available) | 396.4 |
| 4 | 395.6 | 6-(4-cyclopentyl-piperazin-1-yl)-1H-pyrrolo[2,3-b]pyridine-2-carboxylic acid cyclohexylamide | 6-(4-cyclopentyl-piperazin-1-yl)-1H-pyrrolo[2,3-b]pyridine-2-carboxylic acid hydrochloride and cyclohexylamine (commercially available) | 396.4 |
| 5 | 395.6 | azepan-1-yl-[6-(4-cyclopentyl-piperazin-1-yl)-1H-pyrrolo[2,3-b]pyridin-2-yl]-methanone | 6-(4-cyclopentyl-piperazin-1-yl)-1H-pyrrolo[2,3-b]pyridine-2-carboxylic acid hydrochloride and azepane (commercially available) | 396.4 |
| 6 | 395.6 | [6-(4-cyclopentyl-piperazin-1-yl)-1H-pyrrolo[2,3-b]pyridin-2-yl]-(2-methyl-piperidin-1-yl)-methanone | 6-(4-cyclopentyl-piperazin-1-yl)-1H-pyrrolo[2,3-b]pyridine-2-carboxylic acid hydrochloride and 2-methyl-piperidine (commercially available) | 396.2 |
| 7 | 381.5 | 6-(4-yclopentyl-piperazin-1-yl)-1H-pyrrolo[2,3-b]pyridine-2-carboxylic acid cyclopentylamide | 6-(4-cyclopentyl-piperazin-1-yl)-1H-pyrrolo[2,3-b]pyridine-2-carboxylic acid; hydrochloride and cyclopentylamine (commercially available) | 382.4 |
| 8 | 383.5 | [6-(4-cyclopentyl-piperazin-1-yl)-1H-pyrrolo[2,3-b]pyridin-2-yl]-(3-hydroxy-pyrrolidin-1-yl)-methanone | 6-(4-cyclopentyl-piperazin-1-yl)-1H-pyrrolo[2,3-b]pyridine-2-carboxylic acid hydrochloride and 3-hydroxy-pyrrolidine (commercially available) | 384.4 |
| 9 | 409.6 | [6-(4-cyclopentyl-piperazin-1-yl)-1H-pyrrolo[2,3-b]pyridin-2-yl]-(3,5-dimethyl-piperidin-1-yl)-methanone | 6-(4-cyclopentyl-piperazin-1-yl)-1H-pyrrolo[2,3-b]pyridine-2-carboxylic acid hydrochloride and 3,5-dimethyl-piperidine (commercially available) | 410.3 |

TABLE 1-continued

| Ex. No. | MW | Chemical Name | Starting materials | MW found (MH+) |
|---|---|---|---|---|
| 10 | 355.5 | 6-(4-cyclopentyl-piperazin-1-yl)-1H-pyrrolo[2,3-b]pyridine-2-carboxylic acid propylamide | 6-(4-cyclopentyl-piperazin-1-yl)-1H-pyrrolo[2,3-b]pyridine-2-carboxylic acid hydrochloride and propylamine (commercially available) | 356.3 |
| 11 | 392.5 | (S)-1-[6-(4-cyclopentyl-piperazin-1-yl)-1H-pyrrolo[2,3-b]pyridine-2-carbonyl]-pyrrolidine-2-carbonitrile | 6-(4-cyclopentyl-piperazin-1-yl)-1H-pyrrolo[2,3-b]pyridine-2-carboxylic acid hydrochloride and (S)-pyrrolidine-2-carbonitrile (commercially available) | 393.3 |
| 12 | 437.6 | 6-(4-cyclopentyl-piperazin-1-yl)-1H-pyrrolo[2,3-b]pyridine-2-carboxylic acid cyclohexyl-isopropyl-amide | 6-(4-cyclopentyl-piperazin-1-yl)-1H-pyrrolo[2,3-b]pyridine-2-carboxylic acid hydrochloride and cyclohexyl-isopropyl-amine (commercially available) | 438.4 |
| 13 | 383.5 | [6-(4-cyclopentyl-piperazin-1-yl)-1H-pyrrolo[2,3-b]pyridin-2-yl]-morpholin-4-yl-methanone | 6-(4-cyclopentyl-piperazin-1-yl)-1H-pyrrolo[2,3-b]pyridine-2-carboxylic acid hydrochloride and morpholine (commercially available) | 384.4 |
| 14 | 409.6 | [6-(4-cyclopentyl-piperazin-1-yl)-1H-pyrrolo[2,3-b]pyridin-2-yl]-(2-isopropyl-pyrrolidin-1-yl)-methanone | 6-(4-cyclopentyl-piperazin-1-yl)-1H-pyrrolo[2,3-b]pyridine-2-carboxylic acid hydrochloride and 2-isopropyl-pyrrolidine (commercially available) | 410.4 |
| 15 | 395.6 | [6-(4-cyclopentyl-piperazin-1-yl)-1H-pyrrolo[2,3-b]pyridin-2-yl]-(4-methyl-piperidin-1-yl)-methanone | 6-(4-cyclopentyl-piperazin-1-yl)-1H-pyrrolo[2,3-b]pyridine-2-carboxylic acid hydrochloride and 4-methyl-piperidine (commercially available) | 396.4 |
| 16 | 417.5 | [6-(4-cyclopentyl-piperazin-1-yl)-1H-pyrrolo[2,3-b]pyridin-2-yl]-(4,4-difluoro-piperidin-1-yl)-methanone | 6-(4-cyclopentyl-piperazin-1-yl)-1H-pyrrolo[2,3-b]pyridine-2-carboxylic acid hydrochloride and 4,4-difluoro-piperidine (commercially available) | 418.3 |
| 17 | 417.5 | [6-(4-cyclopentyl-piperazin-1-yl)-1H-pyrrolo[2,3-b]pyridin-2-yl]-(3,3-difluoro-piperidin-1-yl)-methanone | 6-(4-cyclopentyl-piperazin-1-yl)-1H-pyrrolo[2,3-b]pyridine-2-carboxylic acid hydrochloride and 3,3-difluoro-piperidine (commercially available) | 418.3 |
| 18 | 411.5 | [6-(4-cyclopentyl-piperazin-1-yl)-1H-pyrrolo[2,3-b]pyridin-2-yl]-(4-methoxy-piperidin-1-yl)-methanone | 6-(4-cyclopentyl-piperazin-1-yl)-1H-pyrrolo[2,3-b]pyridine-2-carboxylic acid hydrochloride and 4-methoxy-piperidine (commercially available) | 412.4 |
| 19 | 397.5 | [6-(4-cyclopentyl-piperazin-1-yl)-1H-pyrrolo[2,3-b]pyridin-2-yl]-(3-hydroxy-piperidin-1-yl)-methanone | 6-(4-cyclopentyl-piperazin-1-yl)-1H-pyrrolo[2,3-b]pyridine-2-carboxylic acid hydrochloride and 3-hydroxy-piperidine (commercially available) | 398.3 |
| 20 | 369.5 | 6-(4-cyclopentyl-piperazin-1-yl)-1H-pyrrolo[2,3-b]pyridine-2-carboxylic acid diethylamide | 6-(4-cyclopentyl-piperazin-1-yl)-1H-pyrrolo[2,3-b]pyridine-2-carboxylic acid hydrochloride and diethylamine (commercially available) | 370.3 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula I:

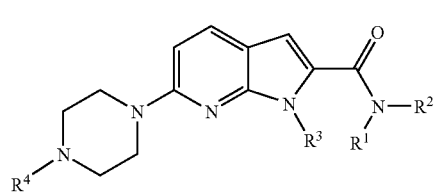

wherein:
$R^1$ is selected from the group consisting of
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl, phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups;

$R^2$ is selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of hydrogen, lower alkyl, lower hydroxyalkyl, lower alkoxyalkyl, lower halogenalkyl, lower cycloalkylalkyl, lower alkanoyl, lower cyanoalkyl, lower alkylsulfonyl, phenylsulfonyl wherein the phenyl ring may be unsubstituted or substituted with one or two groups independently selected from lower alkyl, halogen, lower alkoxy, lower halogenalkoxy and lower hydroxyalkyl, phenyl unsubstituted or substituted with one or two groups independently selected from lower alkyl, halogen, lower alkoxy, lower halogenalkoxy and lower hydroxyalkyl, lower phenylalkyl, wherein the phenyl ring may be unsubstituted or substituted with one or two groups independently selected from lower alkyl, halogen, lower alkoxy, lower halogenalkoxy and lower hydroxyalkyl, and heteroaryl unsubstituted or substituted with one or two groups independently selected from lower alkyl or halogen;

$R^4$ is lower alkyl or cycloalkyl;

and pharmaceutically acceptable salts thereof.

2. The compound according to claim 1, wherein $R^1$ is selected from the group consisting of hydrogen, lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one or two groups independently selected from lower alkyl, lower halogenalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclyl wherein the heterocyclyl ring may be unsubstituted or substituted with one or two lower alkyl groups, and lower heterocyclylalkyl wherein the heterocyclyl ring may be unsubstituted or substituted with one or two lower alkyl groups;

and $R^2$ is hydrogen or lower alkyl.

3. The compound according to claim 1, wherein $R^1$ is lower alkyl or cycloalkyl.

4. The compound according to claim 1, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, a sulfinyl group or a sulfonyl group, said saturated or partly unsaturated heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

5. The compound according to claim 1, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenalkyl, cyano, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

6. The compound according to claim 1, wherein $R^1$ and $R^2$ together with the nitrogen atom to which they are attached form a heterocyclic ring selected from the group consisting of pyrrolidine, piperidine, morpholine and azepane, wherein said heterocyclic ring is unsubstituted or substituted by one, two or three groups independently selected from lower alkyl, halogen, halogenalkyl, cyano, hydroxy, lower alkoxy, oxo, phenyl, benzyl, pyridyl and carbamoyl.

7. The compound according to claim 1, wherein $R^1$ and $R^2$ together with the nitrogen atom to which they are attached form a heterocyclic ring selected from the group consisting of pyrrolidine, 3-hydroxypyrrolidine, 2-cyano-pyrrolidine, 2-isopropylpyrrolidine, morpholine, piperidine, 3-methylpiperidine, 2-methylpiperidine, 3,5-dimethylpiperidine, 3,3-difluoropiperidine, 4,4-difluoropiperidine, 4-methoxypiperidine, 3-hydroxypiperidine and azepane.

8. The compound according to claim 1, wherein $R^3$ is hydrogen.

9. The compound according to claim 1, wherein $R^4$ is cycloalkyl.

10. The compound according to claim 1, wherein $R^4$ is cyclopentyl.

11. The compound according to claim 1, wherein $R^4$ is lower alkyl.

12. The compound according to claim 1, selected from the group consisting of
[6-(4-cyclopentyl-piperazin-1-yl)-1H-pyrrolo[2,3-b]pyridin-2-yl]-piperidin-1-yl-methanone,
[6-(4-cyclopentyl-piperazin-1-yl)-1H-pyrrolo[2,3-b]pyridin-2-yl]-pyrrolidin-1-yl-methanone,
[6-(4-cyclopentyl-piperazin-1-yl)-1H-pyrrolo[2,3-b]pyridin-2-yl]-(3-methyl-piperidin-1-yl)-methanone,
6-(4-cyclopentyl-piperazin-1-yl)-1H-pyrrolo[2,3-b]pyridine-2-carboxylic acid cyclohexylamide,
azepan-1-yl-[6-(4-cyclopentyl-piperazin-1-yl)-1H-pyrrolo[2,3-b]pyridin-2-yl]-methanone,
[6-(4-cyclopentyl-piperazin-1-yl)-1H-pyrrolo[2,3-b]pyridin-2-yl]-(2-methyl-piperidin-1-yl)-methanone,
6-(4-cyclopentyl-piperazin-1-yl)-1H-pyrrolo[2,3-b]pyridine-2-carboxylic acid cyclopentylamide,
[6-(4-cyclopentyl-piperazin-1-yl)-1H-pyrrolo[2,3-b]pyridin-2-yl]-(3-hydroxy-pyrrolidin-1-yl)-methanone,
[6-(4-cyclopentyl-piperazin-1-yl)-1H-pyrrolo[2,3-b]pyridin-2-yl]-(3,5-dimethyl-piperidin-1-yl)-methanone,
6-(4-cyclopentyl-piperazin-1-yl)-1H-pyrrolo[2,3-b]pyridine-2-carboxylic acid propylamide,
(S)-1-[6-(4-cyclopentyl-piperazin-1-yl)-1H-pyrrolo[2,3-b]pyridine-2-carbonyl]-pyrrolidine-2-carbonitrile,
6-(4-cyclopentyl-piperazin-1-yl)-1H-pyrrolo[2,3-b]pyridine-2-carboxylic acid cyclohexyl-isopropyl-amide,
[6-(4-cyclopentyl-piperazin-1-yl)-1H-pyrrolo[2,3-b]pyridin-2-yl]-morpholin-4-yl-methanone,
[6-(4-cyclopentyl-piperazin-1-yl)-1H-pyrrolo[2,3-b]pyridin-2-yl]-(2-isopropyl-pyrrolidin-1-yl)-methanone,
[6-(4-cyclopentyl-piperazin-1-yl)-1H-pyrrolo[2,3-b]pyridin-2-yl]-(4-methyl-piperidin-1-yl)-methanone,
[6-(4-cyclopentyl-piperazin-1-yl)-1H-pyrrolo[2,3-b]pyridin-2-yl]-(4,4-difluoro-piperidin-1-yl)-methanone,
[6-(4-cyclopentyl-piperazin-1-yl)-1H-pyrrolo[2,3-b]pyridin-2-yl]-(3,3-difluoro-piperidin-1-yl)-methanone,
[6-(4-cyclopentyl-piperazin-1-yl)-1H-pyrrolo[2,3-b]pyridin-2-yl]-(4-methoxy-piperidin-1-yl)-methanone,
[6-(4-cyclopentyl-piperazin-1-yl)-1H-pyrrolo[2,3-b]pyridin-2-yl]-(3-hydroxy-piperidin-1-yl)-methanone,
6-(4-cyclopentyl-piperazin-1-yl)-1H-pyrrolo[2,3-b]pyridine-2-carboxylic acid diethylamide,
and pharmaceutically acceptable salts thereof.

13. A process for the manufacture of compounds according to claim 1, comprising the steps of:
coupling a compound of formula II

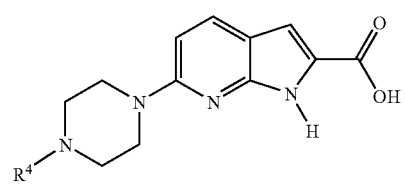

wherein $R^4$ is as defined in claim 1,
with an amine of the formula III

H—NR¹R²    III wherein $R^1$ and $R^2$ are as defined in claim 1,
under basic conditions to obtain a compound of the formula IA

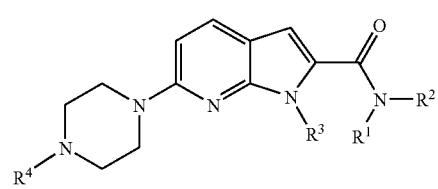

wherein $R^3$ is hydrogen, and optionally transferring into a compound of formula IB

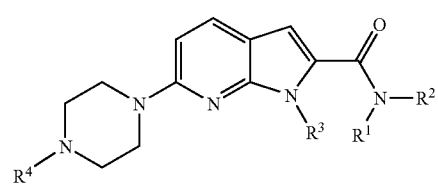

wherein $R^3$ is a group as defined in claim 1 other than hydrogen, and if desired,
converting the compound obtained into a pharmaceutically acceptable acid addition salt.

14. A pharmaceutical composition, comprising a therapeutically effective amount of a compound according to claim 1 as well as a pharmaceutically acceptable carrier and/or adjuvant.

* * * * *